United States Patent [19]

Clark

[11] Patent Number: 5,009,228
[45] Date of Patent: Apr. 23, 1991

[54] DEVICE FOR RELIEVING EAR PAIN

[76] Inventor: Frank L. Clark, 872 E. Napier, Benton Harbor, Mich. 49022

[21] Appl. No.: 371,623

[22] Filed: Jun. 26, 1989

Related U.S. Application Data

[63] Continuation-in-part of Ser. No. 245,577, Sep. 19, 1988, abandoned, which is a continuation-in-part of Ser. No. 161,676, Feb. 29, 1988, abandoned.

[51] Int. Cl.⁵ .............................................. A61F 7/00
[52] U.S. Cl. .................................. 128/380; 128/402; 128/403
[58] Field of Search ..................... 128/379, 380, 399; 165/75, 132; 220/23, 426, 428; 219/385, 387, 439

[56] References Cited

U.S. PATENT DOCUMENTS

| | | | |
|---|---|---|---|
| 1,133,073 | 3/1915 | Venner | 219/438 |
| 1,520,812 | 11/1921 | Eggers | 383/901 |
| 2,191,434 | 10/1939 | Alder | 220/426 |
| 2,526,165 | 6/1947 | Smith | 220/428 |
| 3,322,113 | 5/1967 | Simjian | 219/439 |
| 3,429,369 | 3/1969 | Segal | 220/428 |
| 3,463,161 | 8/1969 | Andrassy | 128/402 |
| 3,545,230 | 8/1970 | Morse | 62/530 |
| 3,746,158 | 7/1973 | Connick | 220/23 |
| 3,766,975 | 10/1973 | Todd | 220/428 |
| 3,796,855 | 3/1974 | Brown et al. | |
| 3,806,701 | 4/1974 | Scott | 219/436 |
| 3,862,451 | 1/1975 | Miller et al. | |
| 3,938,614 | 2/1976 | Ahs | |
| 3,978,233 | 8/1976 | Bolt | 219/387 |
| 4,023,642 | 5/1977 | Korn | |
| 4,344,303 | 8/1982 | Kelly | 62/530 |
| 4,357,809 | 11/1982 | Held | 220/426 |
| 4,408,605 | 10/1983 | Doerr et al. | |
| 4,466,438 | 8/1984 | Katz | |
| 4,478,349 | 10/1984 | Haverland, Jr. et al. | 220/426 |
| 4,572,324 | 2/1986 | Fidi et al. | |
| 4,674,134 | 6/1987 | Lundin | |
| 4,801,782 | 1/1989 | Ineson | 219/438 |

FOREIGN PATENT DOCUMENTS

| | | | |
|---|---|---|---|
| 1195883 | 7/1965 | Fed. Rep. of Germany | 219/439 |
| 2457194 | 6/1976 | Fed. Rep. of Germany | 128/903 |
| 566432 | 9/1957 | Italy | 219/439 |
| 598030 | 3/1948 | United Kingdom | |

Primary Examiner—Edward M. Coven
Assistant Examiner—Mark S. Graham
Attorney, Agent, or Firm—Basile and Hanlon

[57] ABSTRACT

A device for relieving inner ear pain comprised of a cup-shaped housing having a base, an interior adapted to fit over a user's outer ear, a hollow chamber in registry with the base of the cup-shaped member, and a heat dispersing medium disposed in the hollow chamber. A heat generating unit is integrally contained within the housing for heating the heat dispersing medium.

14 Claims, 4 Drawing Sheets

DEVICE FOR RELIEVING EAR PAIN

This application is a continuation-in-part of U.S. Ser. No. 07/245,577 filed on Sept. 19, 1988, abandoned, which is a continuation-in-part of U.S. Ser. No. 07/161,676 filed on Feb. 29, 1988, abandoned.

BACKGROUND OF THE INVENTION

1. Field of the Invention

This invention generally relates to the field of devices for relieving ear pain and, more particularly, to such a device having a heat generating means.

2. Background of the Relevant Art

Ear pain is a wide-spread phenomenon which is attributable to a variety of causes. For example, changes in the air pressure inside an aircraft cabin may adversely affect the passengers therein and inflict ear pain which ranges from the familiar "popping" to severe debilitating pain and sinus pressure. Sometimes the sinus pressure is so acute as to cause bleeding from the nasal cavities for days after the actual pressure changes are encountered. The problem of sudden pressure changes in the cabin is endemic to modern aircraft, regardless of the size and pressurization capacity. Hence, private pilots, as well as the passengers and crew of commercial airliners, may be equally affected by this phenomenon, which is known as "barotrauma". Those occupants of the aircraft who are flying with conditions such as sinusitis, naso-pharyngitis, tonsillitis, rhinitis etc. are particularly prone to develop barotrauma. Likewise, children under the age of seven who have not as yet developed sinuses can suffer ear pain. This problem is especially acute during ascent and descent of the aircraft, when equalization of the pressure between the inner and outer ear is particularly hard to achieve.

Barotrauma is also a phenomenon commonly encountered by underwater divers. Even if a diver is careful to keep his ascent and descent as gradual as possible, the effect of the barotrauma can still be profound, as can be the accompanying pain. Additionally, certain illnesses such as middle ear infections, congestion accompanying the common cold etc. can result in unequal pressure, causing the tympanic membrane to bulge inward. Again, pain is the result.

The idea of applying heat to the outer ear in order to raise pressure in the middle ear, thus causing the tympanic membrane to assume its normal position, is not novel. The problem of barotrauma is dealt with in U.S. Pat. No. 4,408,605. This patent discloses a device for treatment of barotrauma of the middle ear which comprises in combination: a flexible backing portion which is crushable by hand kneading; an annular cushion portion carried by the backing which is shaped and adapted to fit over and enclose the outer ear; and a hand pressure-activated chemical heating package retained by the backing and annular portions. The package contains chemicals in separate compartments which, upon rupture and subsequent mixing of the chemicals by crushing and hand kneading, produces an exothermic reaction. When the device is held over the outer ear, the heat generated by the exothermic reaction is transmitted to the middle ear to treat the barotrauma by reducing the pain and by increasing the volume of the air contained therein. Thus, the device disclosed in the above-listed patent addresses the problem of relieving the ear pain by the application of an analgesic (heat), and by equalizing the inner and outer pressure by the application of the heat.

While the device described in the preceding paragraph may be effective for relieving the pain and other consequences of barotrauma, the device does have certain disadvantages. The hand pressure-activated chemical heating package can be used only one time after which it must be discarded. It is suggested in the disclosure that the device can be constructed to be reusable by sterilizing it and attaching a new chemical packet. However, even the reusable embodiment of the device requires a repeat user to keep a supply of chemical packets on hand. This is inconvenient to the occasional user, and can be an expensive proposition for a regular institutional user such as an airline.

It would be desirable to provide a device for relieving inner ear pain which is entirely reusable and sterilizable, and which does not require the storage of potentially expensive, potentially toxic, chemical packets.

It would also be desirable to provide such a device wherein the heat source may be reused over the life of the device.

SUMMARY OF THE INVENTION

Disclosed and claimed herein is a device for relieving ear pain which comprises a cup-shaped housing having a base and walls forming an interior, a hollow chamber in registry with the base and walls of the cup-shaped member, and a heat source disposed in the hollow chamber. The cup-shaped housing is adapted to fit over a user's outer ear. The heat source disposed in the hollow chamber preferably comprises a heatable liquid, such as water. However, a variety of heat retaining mediums may be used and, more than one type of heat source may be used in a single device, depending on the heat characteristics desired. Alternatively, the heat source may comprise a filler material saturated with liquid, such as gauze packing saturated with water.

Several different embodiments of the herein described invention are contemplated. In one embodiment, the cup-shaped housing is a unitary structure comprised of a resilient, heat-conductive material, such as polypropylene. The hollow chamber further comprises a removable cap. When it is desired to use this embodiment, the cap is removed from the hollow chamber, which is then filled with, for example, hot water. The removable cap is replaced to prevent leakage of the liquid and the user then places the cup-shaped housing over his or her outer ear. Due to the shape of the housing, the outer ear will be positioned adjacent the base of the cup-shaped housing and, hence, near the heat source. Therefore, the temperature of the environment within the outer and middle ear will rise due to the location of the ear with respect to the heat source, and this will cause an increase in pressure, thus serving to relieve the barotrauma. Additionally, the enclosure may be provided with a plurality of ribs disposed on an outer surface of the side wall to prevent the user's fingers from becoming too hot.

Another embodiment discloses means integrally contained within the cup-shaped housing for generating heat. This heat generating means heats up a heat dispersing medium, such as a gel, which is disposed within the housing.

BRIEF DESCRIPTION OF THE DRAWINGS

Various embodiments and exemplifications of the device of the instant invention may best be understood by reference to the following detailed description and drawings in which.

DETAILED DESCRIPTION OF THE PREFERRED EMBODIMENTS

Figure 1:
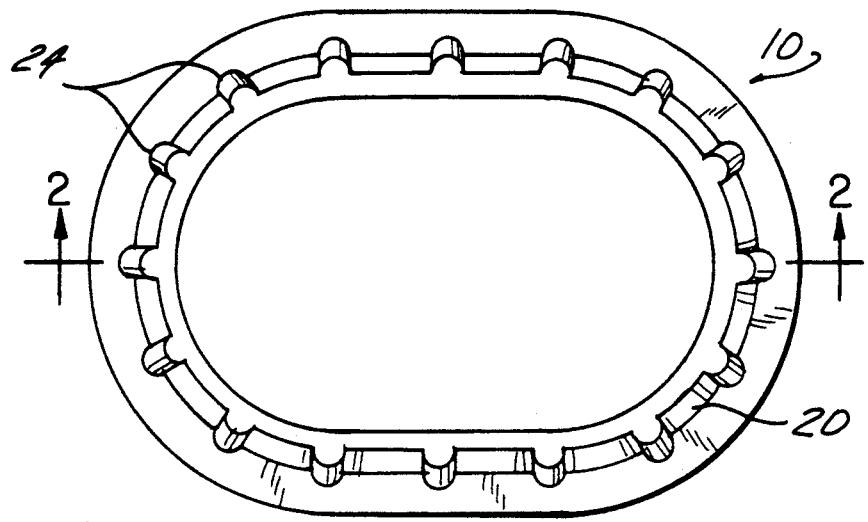
FIG. 1 is a top view of one embodiment of the device of the present invention showing the exterior of the cup-shaped housing.

Throughout the following detailed description, like reference numerals are shown to reference the same feature of the invention shown in multiple embodiments.

Figure 2:
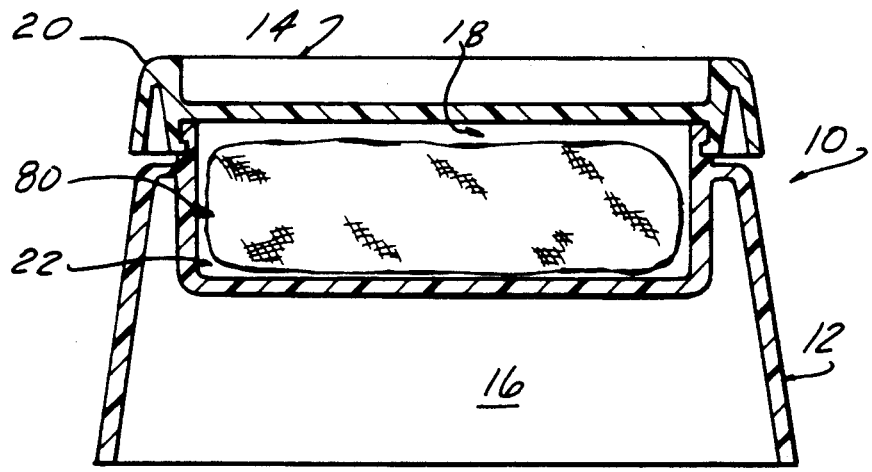
FIG. 2 is a cross-sectional view along lines 2—2 of the device of FIG. 1.
Figure 3:
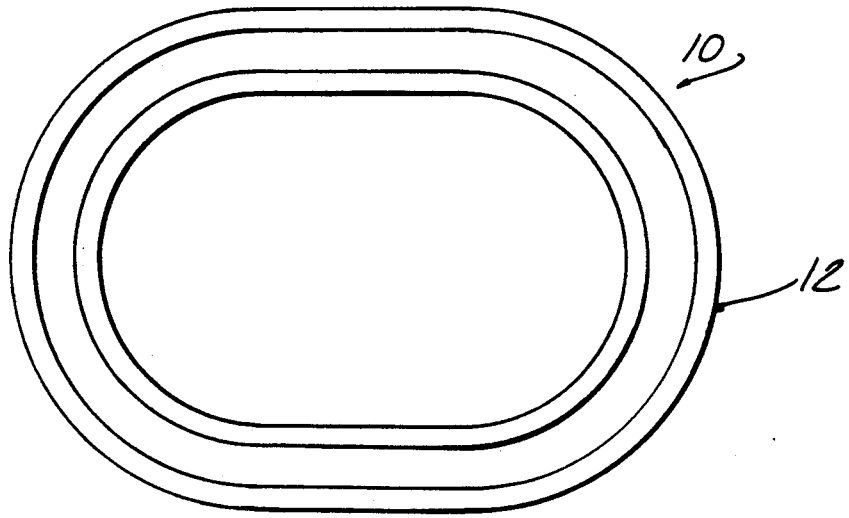
FIG. 3 is a bottom view of the device of FIG. 1 showing the interior of the cup-shaped housing.

Referring now to the drawings, and in particular to FIGS. 1, 2 and 3, there is depicted a device 10 for relieving inner ear pain. The device 10 comprises a cup-shaped housing 12 having a base 14 and an interior 16. The housing 12 is adapted to fit over a user's outer ear. The device 10 further comprises a hollow chamber 18 in registry with the base 14 of the cup-shaped member 12. A heat source 22 is disposed in the hollow chamber 18. The heat source 22 is depicted as a heated liquid, such as hot water. A removable cap 20 prevents egress of the heat source 22 from within the hollow chamber 18. Additionally, the cap 20 may be of a thermally insulative design, to prevent egress of heat, from the device 10 through the cap 20. In a preferred embodiment, the device depicted in FIGS. 1, 2 and 3 is comprised at least partially of a thermally conductive polymeric material, such as polypropylene, but may be constructed of any suitably rigid, thermally conductive material.

As is shown in FIG. 1, the cap 20 may further comprise a plurality of ribs 24 which are disposed peripherally around the outer surface of the cap to prevent the user's fingers from becoming too hot.

Figure 4:
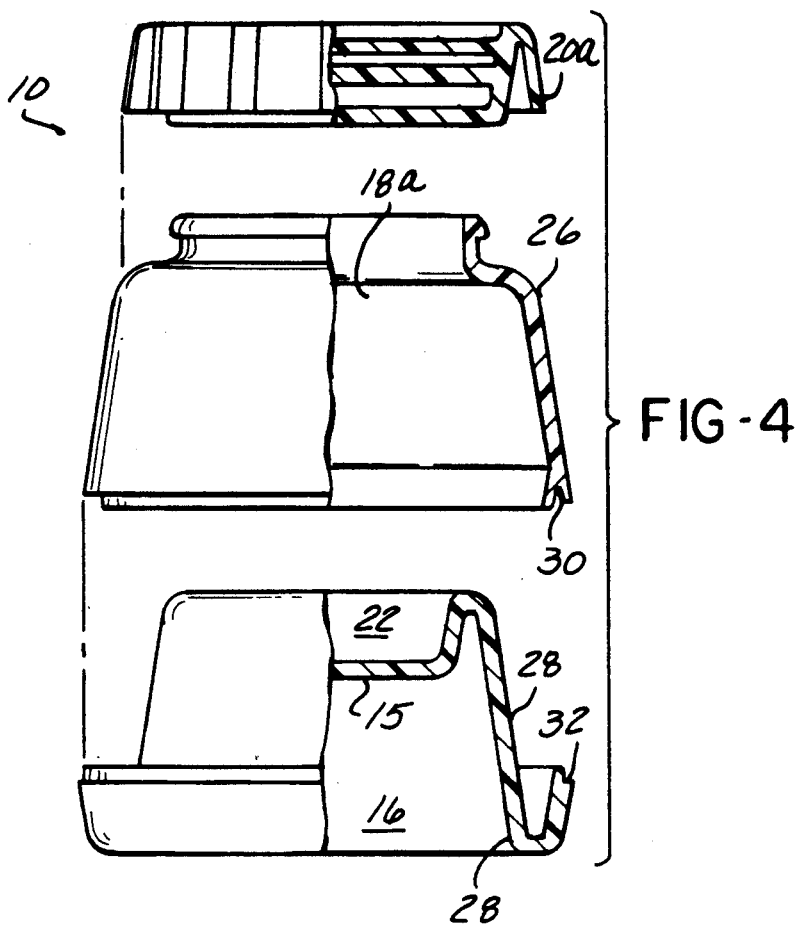
FIG. 4 is a side view, partially in section, of a second embodiment of the device of the present invention prior to assembly.
Figure 5:
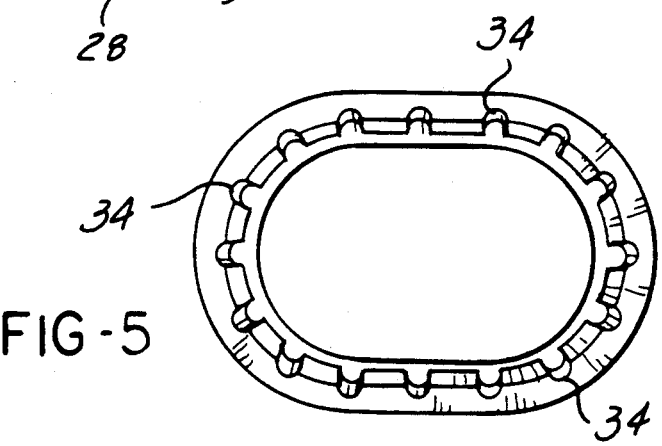
FIG. 5 is a top view of the embodiment of FIG. 4.
Figure 6:
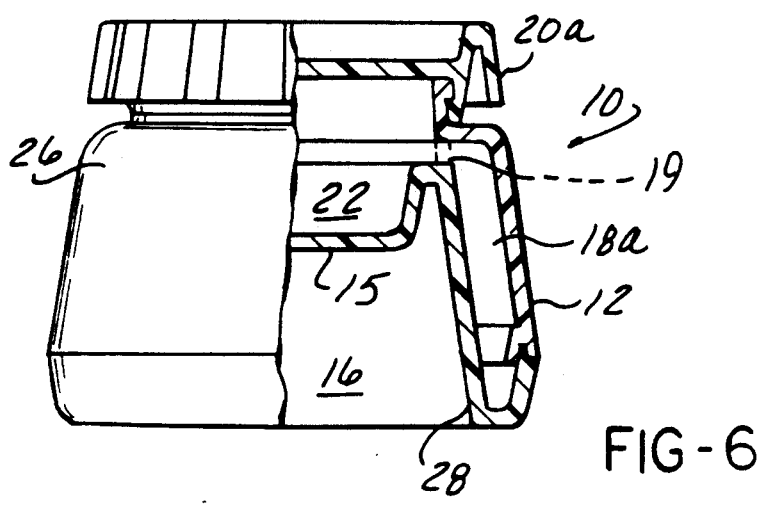
FIG. 6 is a side view, partially in section, of the embodiment of FIG. 4 following assembly.

In a second preferred embodiment, the device 10 depicted in FIGS. 4 through 6, is comprised of several parts, indicated prior to assembly in FIG. 4, which are assembled, as shown in FIGS. 5 and 6, into the completed housing-cap assembly. The device 10 may be comprised at least partially of a thermally conductive polymer material, such as polypropylene, but may be constructed of any suitably rigid, thermally conductive material. The device comprises a first outer housing 26, a second inner housing 28, and a third cap-base 20a. The various parts may be constructed of materials having differing thermal characteristics, dependent upon the desired heat transfer through a given part. For instance, it is desirable to have a high degree of heat transfer through inner housing 28, whereas outer housing 26 should be insulative in nature. The first outer housing 26 is fixedly attached to inner housing 28, by means such as gluing, so as to form a watertight seal along edges 30 and 32 of outer housing 26 and inner housing 28, respectively. Once assembled, as shown in FIG. 6, a hollow chamber 18a is formed between the first outer housing 26 and second inner housing 28. The hollow chamber 18a extends throughout the base area 15 of the interior 16 of the cup-shaped housing 12 and, additionally, extends throughout the walls of the cup-shaped housing 12. In this configuration, the heat source 22 is able to circulate throughout the entire device 10 thus providing an overall uniform heat source 22 which is exposed to the user's ear. Alternatively, hollow chamber 18a may be divided, as by partition 19 shown in phantom, into more than one internal chamber. In this configuration, more than one type of heat source may be used in a single device. By choosing different heat sources having different thermal characteristics, it is possible to vary the nature and duration of the heat transferred to the user's inner ear. A removable cap-base 20a prevents egress of the heat source 22 from within the hollow chamber 18a while also acting as a base for grasping when in use. The removable cap-base 20a may be of a dual wall construction, as shown in FIG. 4, or of other thermally insulative design to prevent egress of heat to the exterior of the device 10 through cap-base 20a. Outer ribs 34 may be disposed about the outer periphery of the cap-base 20a to prevent the user's fingers from becoming too hot.

Figure 7:
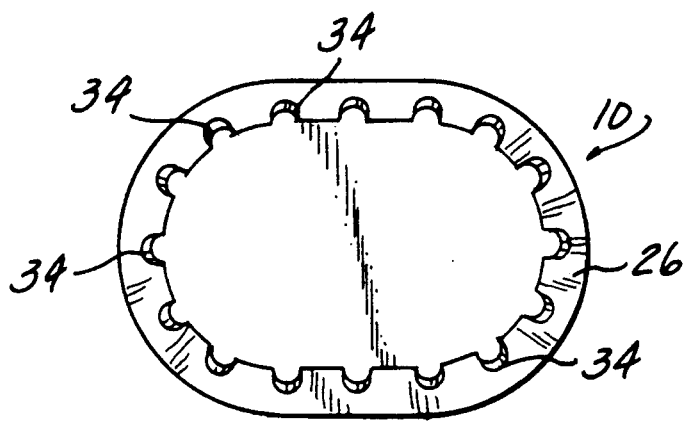
FIG. 7 is a top view of a third embodiment of the device of the present invention.
Figure 8:
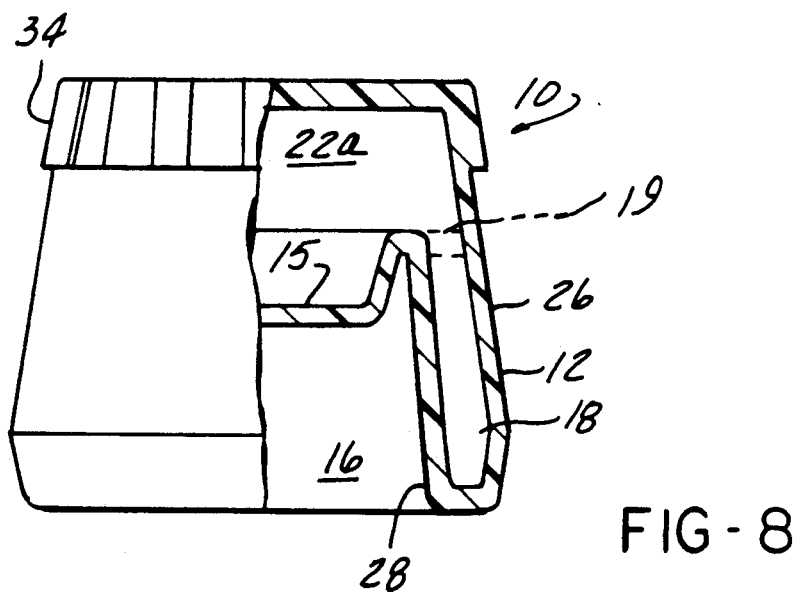
FIG. 8 is a side view, partially in section, of the embodiment of FIG. 7.

In a third preferred embodiment, the device 10 depicted in FIGS. 7 and 8 is comprised of a first outer housing 26 and a second inner housing 28; the outer housing 26 forming a complete enclosure over housing 28, thus eliminating the need for the cap-base 20a as indicated in the second embodiment above. First outer housing 26 is fixedly attached to inner housing 28 by means such as gluing and, once assembled, a hollow chamber 18 is formed between the housings. A heat source 22a is permanently installed within chamber 18 and is designed to allow the user to reheat the permanent heat source 22a by placing the device 10 in a microwave oven or other source of heat, such as boiling water. As described above, hollow chamber 18 may be subdivided should it be desirable to employ more than one type of heat source therein. This embodiment disposes with the need for transferring the heat source prior to use. The device 10 may be comprised, at least partially, of a polymeric material, such as polypropylene, but may be constructed of any suitable, rigid, thermally conductive material. Outer ribs 34 may be disposed about the outer periphery of housing 26 to prevent the user's fingers from becoming too hot.

Figure 9:
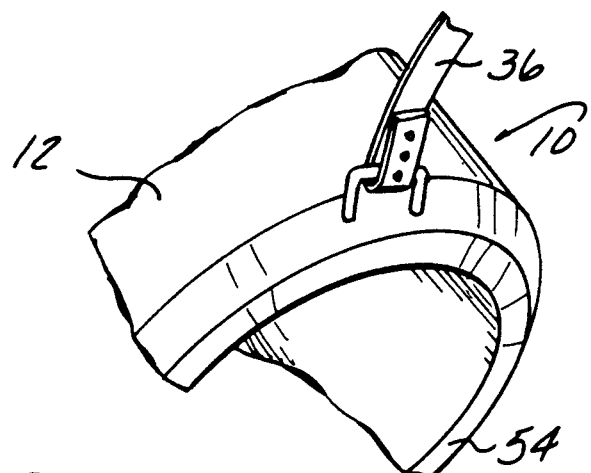
FIG. 9 is a partial perspective view of the device of the present invention with an optional retaining strap installed.

In all of the above embodiments, a strap 36, indicated in FIG. 9, may be provided which is used to hold the device 10 over the ear without the necessity of holding the cup with the hand. Such a strap 36 is beneficial in cases when the user will be reclining or attempting to sleep.

Figure 10:
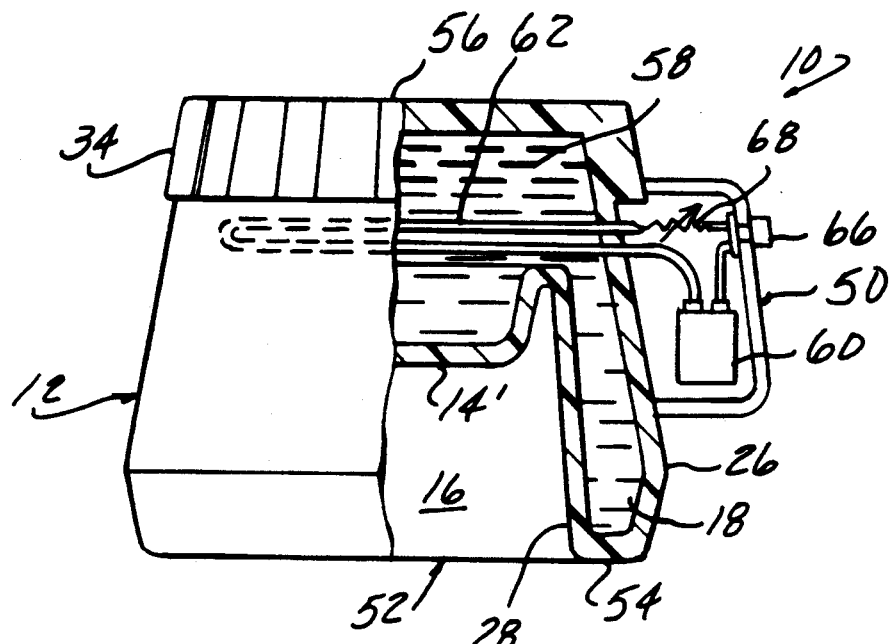
FIG. 10 is a side view, partially in section, of a fourth embodiment of the device of the present invention.

In any of the above embodiments, means 50 for generating heat may be added, as shown in FIG. 10. Device 10 comprises a generally cup-shaped housing 12 of dual wall construction, having inner walls 28, and outer walls 26. Device 10 further comprises a base portion 14' and an open end portion 52. The dual wall 26, 28 are enclosed to define a heat chamber 18, which extends through the walls 26, 28 and the base portion 14'. An ear enclosing chamber 16 is defined by the inner wall 28 and open end portion 52 of the housing 12. The ear enclosing chamber 16 has a wide, smooth annular portion 54, as can also be seen in FIG. 9, extending about the perimeter of the open end portion 52 for tight and comfortable contact with the side of the user's head when the housing 12 is in place over the user's ear. An upper member 56 forms the outer wall 26 of the base portion 14'. Upper member 56 may be part of a unitary structure as is shown in FIG. 10, or it may be comprised of the cap base 20, 20a, as is shown in FIGS. 2 and 6. Upper member 56 may be in a permanent water-tight relationship with the housing 12. If a cap 20, 20a is used, this may be removable or it also may be sealed such that it is similarly in a permanent water-tight relationship with the housing 12.

A heat dispersing medium 58 is disposed within housing 12. The heat dispersing medium 58 may be comprised of any suitable medium which will thoroughly and efficiently conduct heat through heat chamber 18 and into the ear enclosing chamber 16. In the preferred embodiment, this heat dispersing medium 58 is a phase-change salt or oil, such as a carboxymethylcellulose mixture or a mineral or similar material.

Suitable phase-change salts are those that will store energy and release it while maintaining an essentially constant temperature. Preferably the phase-change salt is a solid block which will melt when exposed to elevated temperatures to store heat energy while remaining cool to touch. When activated by a suitable activation media such as a metal strip or the like, the phase-change salt will release heat energy as it resolidifies. Energy release will continue for a period of 10-20 minutes with a temperature generation between 120° and 130° F.

Figure 11:
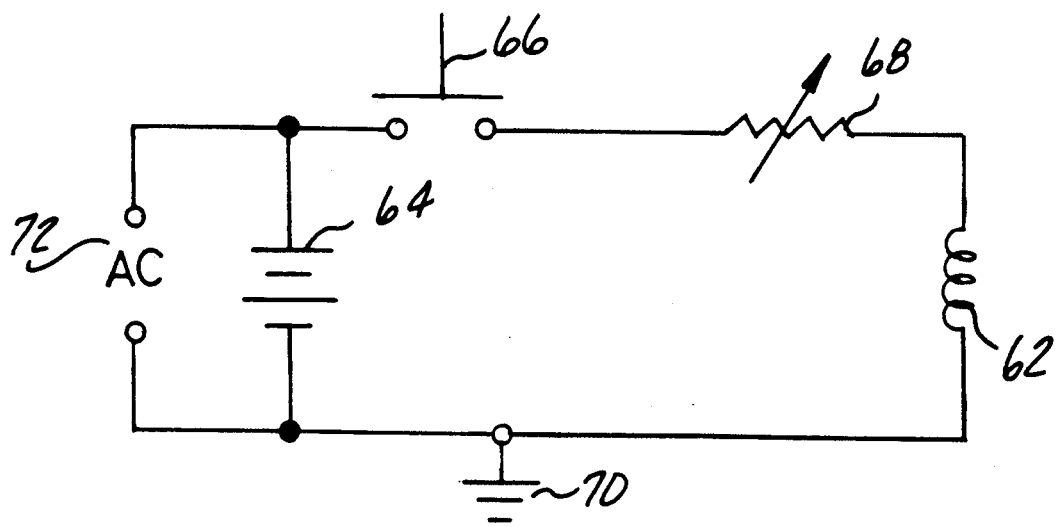
FIG. 11 is a schematic diagram showing the circuit of the embodiment shown in FIG. 10.

Means 50 are integrally contained within housing 12 for generating heat. The heat generating means 50 comprises an electric power source 60 and a coil 62 connected to power source 60. Coil 62 may be any length or configuration of micro wires, i.e., straight, looped, etc. One of ordinary skill in the art will be able to determine the length and configuration needed to heat the heat dispersing medium 58. Power source 60 may comprise a D.C. source, such as a battery, or an A.C. source. If an A.C. source is used, proper rectification means must be used in order to convert the standard A.C. voltage to the proper D.C. voltage. Shown in FIG. 11 is a circuit diagram for the device 10, shown in FIG. 10. Battery 64 is connected to switch means 66. Means 66 is switchable between first and second positions to selectively apply power from battery 64 to coil 62. Means 68 for variably resisting the amount of current may be provided between switch means 66 and coil 62. Resisting means 68 may be used to selectively vary the amount of current passed through coil 62, thus determining the amount of heat given off. Ground 70 is connected between coil 62 and battery 64. If A.C. voltage 72 is used, battery 64 is bypassed, and the voltage runs through proper rectification (not shown) before passing through resisting means 68 and coil 62. Switch means 66 need not be used with A.C. voltage 72, since the act of plugging device 10 into a wall outlet can act as a switch.

To use the device 10, the cap 20, 20a is removed from hollow chamber 18, 18a. A heat source 22, such as hot water, is placed within the hollow chamber and the cap 20, 20a is replaced. Alternately, the device 10, described above, having a permanent heat source 22a, may be placed in a microwave oven or boiling water thereby heating heat source 22a to a usable temperature. This method is particularly preferred for use with devices containing phase-change salts as the heating medium. Alternately, device 10, having heat dispersing medium 58, may be switched on and plugged into a wall outlet or run off a battery 64 in order to run current through the coil 62, which will thereby heat the heat dispersing medium 58 to a usable temperature. The cup-shaped housing 12 is placed over the user's outer ear allowing heat from heat source 22 or heat dispersing medium 58 to be radiated into the interior 16 of the cup-shaped housing 12, and to the ear which is disposed within the interior 16. This radiation of heat will cause the air pressure in the user's middle ear to become equalized with the surrounding atmosphere, thus serving to quickly relieve the pain and distress caused by barotrauma.

In all the described embodiments, the heat source 22 may comprise a filler material 80 saturated with liquid, such as gauze packing saturated with water, as shown in FIG. 2.

While certain embodiments of the invention have been described in detail above in relation to devices for relieving inner ear pain, it will be apparent to those skilled in the art that the disclosed embodiment may be modified. Therefore, the foregoing description is to be considered exemplary rather than limiting, and the true scope of the invention is that defined in the following claims.

What is claimed is:

1. A treatment device for use in conjunction with the outer ear and surrounding cranial base region of a patient for relieving inner ear pain, the device comprising:
   a cup-shaped housing having an oval shape to conform to the shape of the outer ear for closely enclosing the outer ear, said cup-shaped housing having a base and wall means, said wall means having an outer edge and said base and wall means defining a first interior chamber enclosed by said wall means and said base, said outer edge of said wall means for contacting the surrounding cranial region of the patient and said housing being adapted to fit over the patient's outer ear to define an insulated treatment region;
   a second hollow chamber in registry with the base of the cup-shaped member, the second hollow chamber being subdivided into multiple individual chambers; and
   a reusable heat source disposed within said second hollow chamber;
   wherein each of said multiple individual chambers contains a different heat source, each of said different heat sources having differing thermal characteristics.

2. A treatment device for use in conjunction with the outer ear and surrounding cranial base region of a patient for relieving inner ear pain, the device comprising:
   a cup-shaped housing having a base and wall means, said wall means having an outer edge and said base and wall means defining a first interior chamber enclosed by said wall means and said base, said outer edge of said wall means for contacting the surrounding cranial region of the patient and said housing being adapted to fit over the patient's outer ear to define an insulated treatment region;
   a second hollow chamber in registry with the base of the cup-shaped member; and a reusable heat source comprising a filler material saturated with liquid disposed within said second hollow chamber.

3. A treatment device for use in conjunction with the outer ear and surrounding cranial base region of a patient for relieving inner ear pain, the device comprising:
   a cup-shaped housing having a base and wall means, said wall means having an outer edge and said base and wall means defining a first interior chamber enclosed by said wall means and said base, said outer edge of said wall means for contacting the surrounding cranial region of the patient and said housing being adapted to fit over the patient's outer ear to define an insulated treatment region;
   a second hollow chamber in registry with the base of the cup-shaped member;
   a reusable heat source disposed within said second hollow chamber; and
   an adjustable strap, attached to opposite sides of said cup-shaped housing adaptable to be fit around the patient's head, to hold said housing in place over the patient's ear.

4. A treatment device for use in conjunction with the outer ear and surrounding cranial base region of a patient for relieving inner ear pain, the device comprising:
   a cup-shaped housing at least partially comprised of a thermally conductive, rigid material, the housing having a base and wall means, said wall means having an outer edge and said base and wall means defining a first interior chamber enclosed by said wall means and said base, said outer edge of said wall means for contacting the surrounding cranial region of the patient and said housing being adapted to fit over the patient's outer ear to define an insulated treatment region;
   a second hollow chamber in registry with the base of the cup-shaped member;
   a reusable heat source disposed within said second hollow chamber; and
   an adjustable strap, attached to opposite sides of said cup-shaped housing adaptable to be fit around the patient's head, to hold said housing in place over the patient's ear.

5. A device for use in conjunction with the outer ear and surrounding cranial base region of a patient for relieving inner ear pain, the device comprising:
   a cup-shaped housing having an oval shape to conform to the shape of the outer ear for closely enclosing the outer ear, said cup-shaped housing defining a first ear enclosing interior chamber, said interior chamber having a first open end portion and a second base portion, said first open end portion configured to closely encompass the outer ear of the user, said cup-shaped housing further comprising inner and outer walls defining a second heat chamber therebetween, an opening formed in said outer wall at said second base portion, and an annular portion means, extending around the perimeter of said first open end portion, for tightly and comfortably contacting the side of a user's head;
   a removable cap, engageable over, and in a water tight relationship with, said opening in said outer wall, and configured to provide a flat base for grasping when in use; and
   a heat source within said second heat chamber for heating said first ear enclosing interior chamber and the inner ear of the user when said cup-shaped housing is placed over the outer ear.

6. The device for relieving ear pain, as defined in claim 5, wherein said removable cap is insulated to prevent egress of heat.

7. The device for relieving ear pain, as defined in claim 5, further comprising a plurality of longitudinally extending raised ribs extending about the periphery of said removable cap for protecting the user's fingers from excessive heat during use.

8. The device for relieving ear pain, as defined in claim 5, wherein said heat source comprises a heated liquid.

9. A device for use in conjunction with the outer ear and surrounding cranial base region of a patient for relieving inner ear pain, the device comprising:
   a cup-shaped housing, defining a first ear enclosing interior chamber, said interior chamber having a first open end portion and a second base portion, said first open end portion configured to closely encompass the outer ear of the user, said cup-shaped housing further comprising inner and outer walls defining a second heat chamber therebetween, an opening formed in said outer wall at said second base portion, and an annular portion means, extending around the perimeter of said first open end portion, for tightly and comfortably contacting the side of a user's head;
   a removable cap, engageable over, and in a water tight relationship with, said opening in said outer wall, and configured to provide a flat base for grasping when in use; and
   a filler material saturated with heated liquid disposed within said second heat chamber for heating said first ear enclosing interior chamber and the inner ear of the user when said cup-shaped housing is placed over the outer ear.

10. A device for use in conjunction with an ear of a patient for applying heat from a heat source to the ear of the patient, the device comprising:
   a generally cup-shaped housing of dual wall construction, having an inner wall and an outer wall, a base portion, and an open end portion, said dual walls being enclosed to define a heat chamber in which the heat source is placed, said heat chamber extending through said walls and said base portion, said cup-shaped housing having an oval shape to conform to the shape of the outer ear for closely enclosing the outer ear;
   a removable end cap, forming the outer wall for said base portion, engageable with said housing in a watertight relationship and removable for access to said heat chamber;
   an ear enclosing chamber defined by the inner walls of said cup shaped housing, having an open end portion means for encompassing the patient's ear within said ear enclosing chamber, and having an annular portion means, extending about the perimeter of said open end portion, for tight and comfortable contact with the side of the patient's head when said housing is in place over and closely encompasses the patient's ear;
   wherein the heat source disposed within said heat chamber heats said ear enclosing chamber and the ear of the patient.

11. The device for applying heat from a heat source to the inner ear of a user, as defined in claim 10, wherein said removable end cap is insulated to prevent egress of heat.

12. The device for applying heat from a heat source to the inner ear of a user, as defined in claim 10, further comprising a plurality of raised ribs on an exterior perimeter surface of said removable cap for protecting the user's fingers from excessive heat during use.

13. The device for applying heat from a heat source to the inner ear of a user, as defined in claim 10, wherein a heated liquid is placed in said heat chamber.

14. A device for use in conjunction with an ear of a patient for applying heat from a heat source to the ear of the patient, the device comprising:
- a generally cup-shaped housing of dual wall construction, having an inner wall and an outer wall, a base portion, and an open end portion, said dual walls being enclosed to define a heat chamber in which the heat source is placed, said heat chamber extending through said walls and said base portion;
- a removable end cap, forming the outer wall for said base portion, engageable with said housing in a watertight relationship and removable for access to said heat chamber;
- an ear enclosing chamber defined by the inner walls of said cup shaped housing, having an open end portion means for encompassing the patient's ear within said ear enclosing chamber, and having an annular portion means, extending about the perimeter of said open end portion, for tight and comfortable contact with the side of the patient's head when said housing is in place over and closely encompasses the patient's ear;
- wherein the heat source comprises a filler material saturated with heated liquid disposed in said heat chamber, and wherein said filler material heats said ear enclosing chamber and the ear of the patient.

* * * * *